United States Patent [19]

Abbott et al.

[11] Patent Number: 4,521,521
[45] Date of Patent: Jun. 4, 1985

[54] PARTICLE REAGENT SIZE DISTRIBUTION MEASUREMENTS FOR IMMUNOASSAY

[75] Inventors: Scot D. Abbott, Wilmington, Del.; Michael A. G. Luddy, West Chester, Pa.

[73] Assignee: E. I. Du Pont de Nemours and Company, Wilmington, Del.

[21] Appl. No.: 474,483

[22] Filed: Mar. 11, 1983

[51] Int. Cl.³ .............................................. G01N 33/54
[52] U.S. Cl. .................................... 436/517; 250/574; 356/336; 356/337; 436/533; 436/534; 436/805; 436/807; 436/817
[58] Field of Search ................ 250/574; 356/341, 336, 356/337; 436/517, 533, 534, 805, 807

[56] References Cited

U.S. PATENT DOCUMENTS

| | | | |
|---|---|---|---|
| 4,080,264 | 3/1978 | Cohen et al. | 195/103.5 A |
| 4,157,871 | 6/1979 | Anderson | 436/805 X |
| 4,174,952 | 11/1979 | Cannell et al. | 23/230 B |
| 4,184,849 | 1/1980 | Cambiaso et al. | 23/230 B |
| 4,191,739 | 3/1980 | Uzgiris et al. | 424/12 |
| 4,279,617 | 7/1981 | Masson et al. | 23/230 B |
| 4,305,665 | 12/1981 | Achter | 356/339 |
| 4,446,239 | 5/1984 | Tsuji | 436/532 |

*Primary Examiner*—Sidney Marantz

[57] ABSTRACT

A highly sensitive and rapid method for quantitatively assaying analytes in liquid media by directly measuring changes in particle size distribution of reagent particles having analyte insolubilized thereon in a system undergoing antibody-induced aggregation has been developed. The amount of analyte initially present can be determined by measuring the change in the distribution of particle size with time, the concentration of a particular size particle at a given time, the rate of formation of a particular size particle, or the steady-state maximum concentration for a particular size particle.

11 Claims, 6 Drawing Figures

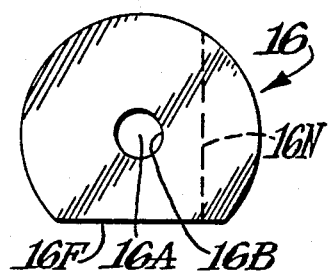
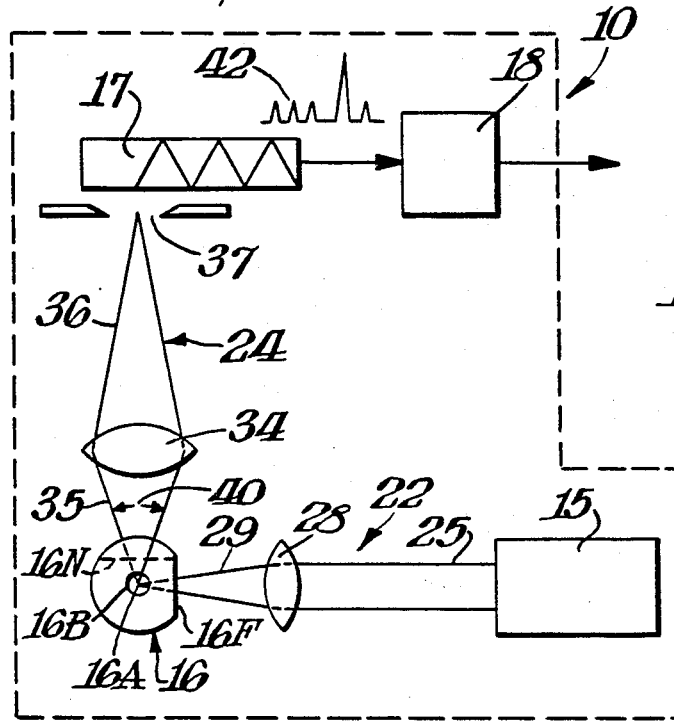
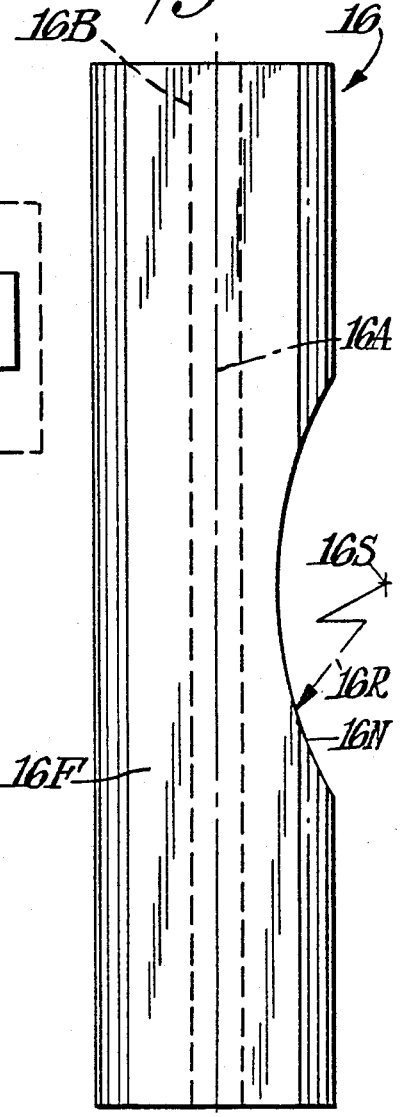

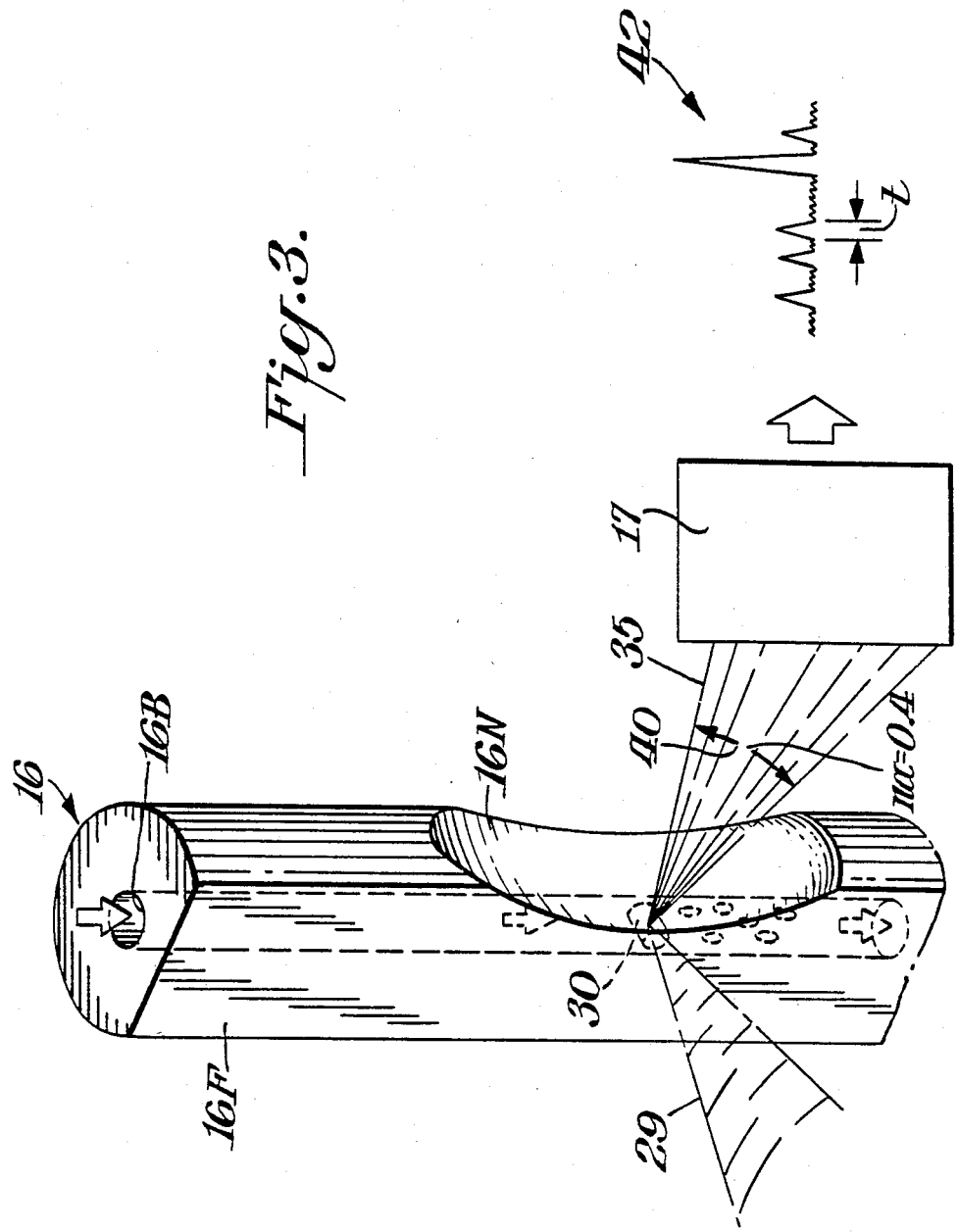

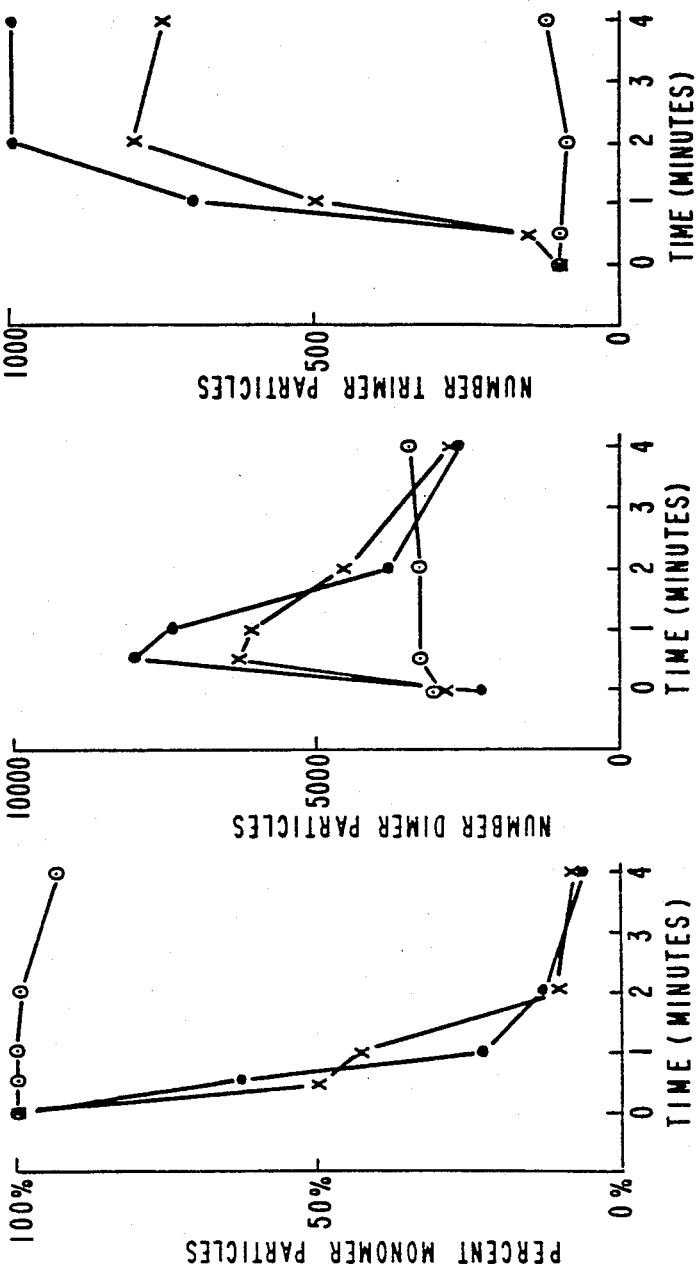
FIG. 5 KINETIC ANALYSIS OF PARTICLE AGGREGATION FOR VARIOUS DIGOXIN CONCENTRATIONS

PARTICLE REAGENT SIZE DISTRIBUTION MEASUREMENTS FOR IMMUNOASSAY

TECHNICAL FIELD

This invention relates to a highly sensitive and rapid method for quantitatively assaying analytes in liquid media by directly measuring changes in the distribution of particle sizes in an aggregating system comprising particle reagent with surface bound analyte, analyte specific antibody, and analyte from the test sample. Inhibition of the aggregation of particles by antibody, caused by competing reactions of antibody with analyte, can be accurately measured by laser light scattering instrumentation and selective particle counting procedures as a function of time after contacting the reagents.

RELATED APPLICATIONS

Subject matter disclosed herein is disclosed in the copending application of S. D. Abbott et al. titled "Particle Counting Apparatus", U.S. patent application Ser. No. 474,482 filed contemporaneously herewith.

BACKGROUND OF THE INVENTION

Clinical laboratory chemical diagnostic tests are an important component of health care delivery. The utilization of these tests by physicians to monitor drug levels where only a narrow therapeutic range exists, to guide decisions on treatment and surgical options, and to screen patients for the early detection of disease has rapidly increased the number of tests performed annually. With almost 6 billion tests performed in 1976 and 12.2 billion estimated to be performed in 1986 [Luning Prak Associates Survey, 1980], speed, accuracy, and cost control are important objectives. The desire to measure such analytes as drugs, hormones, and metabolites at micromolar ($\mu$M) to picomolar (pM) levels in complex body fluid matrices has led to the development of sophisticated test methodology which can be implemented by automated techniques at reasonable cost.

Broadly applicable, accurate screening assays are therefore needed to monitor the presence and quantity of biological materials. Various methods have been utilized in the past including liquid and gas chromatography, mass spectrometry, and numerous bioassay techniques. These methods are time consuming and not easily applied in large-scale, automated screening programs.

In recent years, a number of immunoassay techniques have been developed to take advantage of the specificity of antibody reactions while avoiding the complicating features of radiochemical labelling. Agglutination reactions involving bivalent antibodies and antigens or haptens of clinical interest have been utilized in both visual and quantitative assays with a wide variety of bacteria, red blood cells, or polymer particles. Agglutination results from the growth of antibody-antigen bridged particle aggregates to produce an extensive network which can be detected. Agglutination can result by adding the specific binding partner, either antibody or antigen, to the suspension of particles with immobilized antigen or antibody. At low concentrations of the specific binding partner, small aggregates consisting only of a few particles are produced. The presence of both free and particle-immobilized reagent results in an inhibition of aggregation by the specific binding partner.

Several systems of clinical analysis have been developed using particle immobilized reagents which generally provide specificity through their method of preparation, and quantitative information from the aggregation kinetics obtained in the presence of the analyte of interest. In these systems, the analyte of interest constitutes the antigen or hapten against which specific binding antibody is prepared. Particle-based reagent systems can provide a sensitive, flexible measurement system for quantifying such medically important materials as cardiac glycosides, antibiotics, therapeutic drugs, hormones, and vitamins. In addition, methods of analysis for toxins, food and packaging additives and environmental pollutants at low concentrations are required.

U.S. Pat. No. 4,174,952, issued to Cannell et al., discloses a particle-based immunoassay measurement method in which the ratio of intensity of light scattered at two different angles, the so-called anisotropy ratio, is determined as a relative measure of the distribution of particle sizes. This method requires the use of initially monodisperse particle reagents in order to detect a change in the anisotropy ratio at low levels of aggregation. A broad distribution of particle sizes, as generally found in a polymer latex, would have low sensitivity for detection of analyte or antibody induced aggregates because only a small change in the anisotropy ratio will be observed. Similarly, the method is primarily useful during the early stages of aggregation where the rate of change of the anisotropy ratio is great.

U.S. Pat. No. 4,184,849, issued to Cambiaso et al. discloses a method of particle-based immunoassay utilizing selective counting techniques with two different particulate reagents. The particles in this case are required to be at least a factor of two different in size, and each particle suspension must be uniform in size. The technique involves a measurement of the fraction of unaggregated (monomer) particles of one size in the system. The measurement of the disappearance of unaggregated particles requires long incubation times, however.

U.S. Pat. No. 4,191,739, issued to Uzgiris et al. discloses the use of a mixture of two antibody-coated latex particle suspensions to measure analyte concentration. The choice of particle sizes is, however, critical requiring a particle volume ratio of about 1.5:1 for the two particles. The assay is based upon counting particles of a size which would not exist but for an antigen-antibody interaction. The system must therefore be carefully designed with respect to particle size and requires relatively sophisticated electronic equipment to carry out the measurements.

U.S. Pat. No. 4,080,264, issued to Cohen et al. discloses a particle-based immunoassay technique utilizing quasi-elastic light scattering. Direct measurement of the mean diffusion coefficient of the particles can be related to particle size through the Einstein and Stokes equations. The presence of target analyte in the medium leads to aggregation and an increase in particle size which is related to analyte concentration. In general, however, the technique is utilized only with uniform-sized particle latex suspensions and reserved for measurements in the early stages of interaction where there is a large change in the mean diffusion coefficient. Analysis of the data also requires an assumption about the distribution of particle aggregate sizes present.

U.S. Pat. No. 4,279,617 issued to Masson et al. discloses a two-particle immunoassay and selective particle counting to analyze human sera for small quantities of antibodies indicating allergy, infection, or autoimmune diseases. The method only monitors the concentration of unaggregated first or second particulate reagent, and requires that one of the two particle reagents be of particle size at least 0.6 micrometer or greater to obtain reliable particle counting.

SUMMARY OF THE INVENTION

There exists a clear need for improved, low cost methods utilizing particle-based immunochemical assays which are sensitive, rapid and can be automated. In particular, a method capable of utilizing nonuniform-sized polymer particle reagent suspensions containing particles whose average diameter is as small as 0.1 micrometer to obtain large particle diffusion coefficients is required to provide fast, accurate clinical analyses. Such a method would not require the use of expensive, limited production monodisperse polymer particle suspensions.

A novel, selective particle counting immunoassay method has been discovered which allows the use of nonuniform sized latex particle reagent suspensions, even those initially containing some aggregated material. This method involves the determination of the distribution of particle sizes by actual measurement of the number of particles in given size ranges present in the test sample as a function of time as the particle reagent undergoes aggregation in the presence of analyte-specific antibody and analyte. Knowledge of the actual distribution of particle sizes under test conditions can be correlated with the amount of analyte initially present in the test sample by a variety of techniques including measurement of (1) the change in the distribution of particle size with time, (2) the concentration of a given size particle at a given time, (3) the rate of formation of a given size particle, or (4) the steady-state maximum concentration of a given size particle. Specifically, this invention involves a method for determining the amount of an analyte in liquid medium comprising the steps of:

A. Contacting said liquid medium with reagents including:
  (1) analyte specific antibody, and
  (2) particle reagent coated with insolubilized analyte to form an aggregating reaction mixture;
B. passing said reaction mixture through an optically defined viewing zone upon which focused laser radiation is incident;
C. collecting the scattered laser radiation from said reaction mixture; and
D. analyzing said scattered laser radiation to determine the particle size distribution in said reaction mixture as a function of time subsequent to contacting said liquid medium with said reagents thereby determining the amount of said analyte initially present in said liquid medium.

BRIEF DESCRIPTION OF THE DRAWINGS

The invention will be more fully understood from the following detailed description thereof taken in connection with the accompanying drawings which form a part of this application and in which:

FIG. 1 is a stylized pictorial representation of a particle counting system in accordance with the present invention;

FIGS. 2A and 2B are, respectively, plan and side elevational views of a cuvette adapted for use in a particle counting apparatus in accordance with the present invention;

FIG. 3 is a stylized schematic representation of the scattering and collection of radiation by particles passing through a viewing zone in a cuvette such as that shown in FIG. 2;

FIG. 5 is a series of plots of the percent of particles present or of the number of particles present as a function of time for monomer, dimer, and trimer particles for various digoxin concentrations.

DETAILED DESCRIPTION OF THE INVENTION

Figure 4:
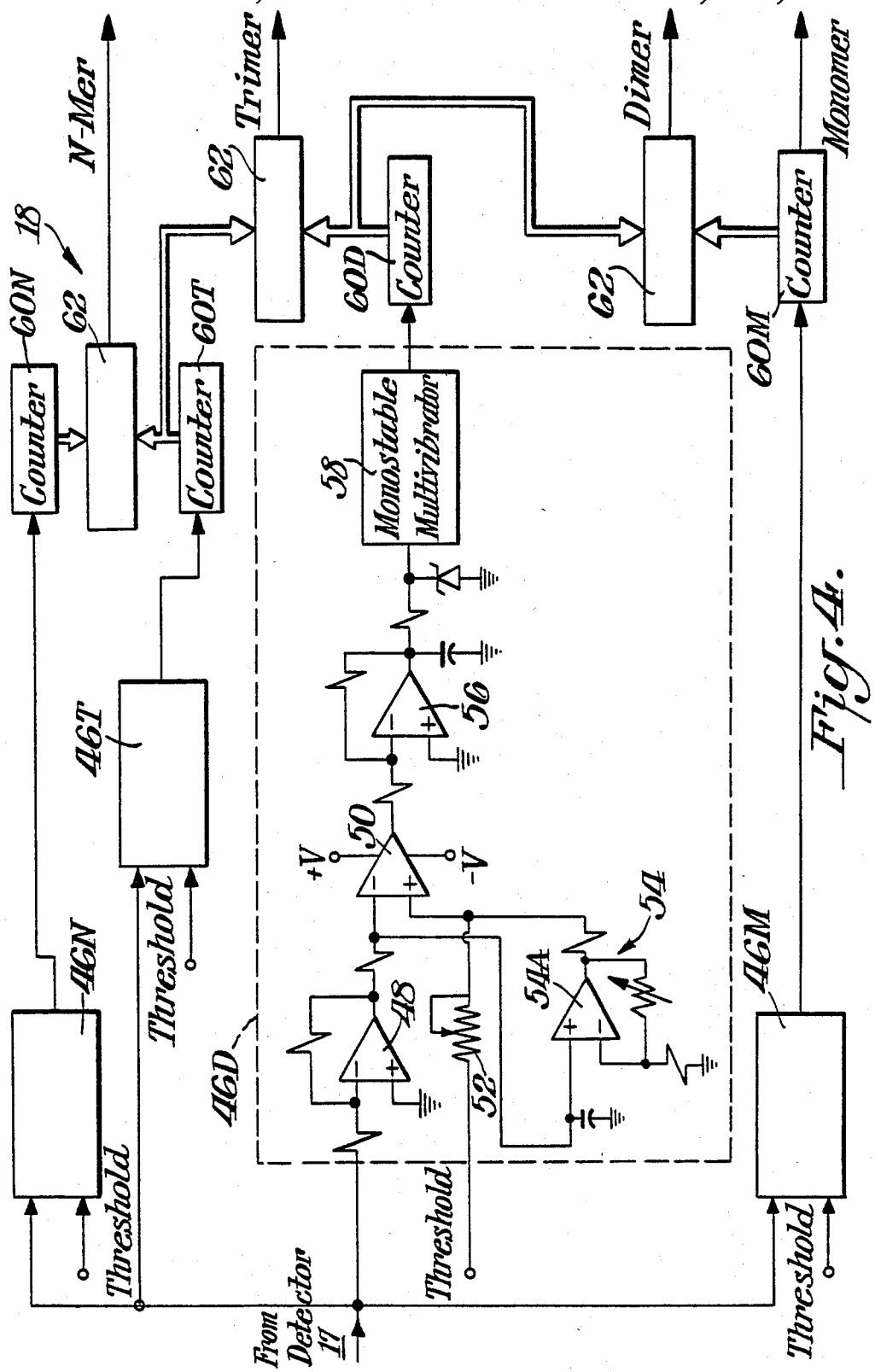
FIG. 4 is a schematic diagram of an electrical circuit adapted for use in a particle counting apparatus according to the present invention.

Light scattering and selective particle counting techniques have been utilized to develop an extremely sensitive and versatile immunochemical assay method. The process directly measures the number of monomer particles as well as dimer, trimer, and N-mer particle aggregates as a function of time after contacting particle reagent, analyte-specific antibody, and test sample. The experimental system for detecting and counting such particles having sizes as small as 0.1 micrometer incorporates a source of collimated radiation at a given wavelength, preferably a laser, which illuminates a cuvette with an optically defined viewing zone of about $10^{-12}$ liter through which the fluid suspension containing both aggregated and individual particles flows. A detector, responsive to the intensity of radiation scattered by each particle in the stream, generates an electrical signal functionally related to the size of the particle. A counter network operatively associated with the detector registers a count of the number of particles in the stream that fall within a predetermined size range.

The approach of the instant invention based on using particulate reagents in conjunction with selective particle counting offers several advantages for immunochemical analyses. Nonuniform size particulate reagents can be utilized which are less expensive and more readily available than monodisperse suspensions. Knowledge of the distribution of particle sizes (the number of monomer, dimer, trimer, and N-mer particles per unit volume) as a function of time precludes an ambiguity which conceivably might result from small dimer particles being counted as monomer particles. Selective particle counting provides enhanced measurement sensitivity at short aggregation times since one can follow the rate of formation of dimer particles. Turbidimetric measurements, on the other hand, require large aggregates and are therefore best suited to advanced stages of aggregation. Selective particle counting to directly measure the concentration of various size particles thus provides flexibility to deal with a variety of particle reagents and measurement times.

In the context of this disclosure, the following terms shall be defined as follows: "analyte" is the substance, or group of substances, whose presence or amount in liquid medium is to be determined; "particle reagent" is a core polymer particle with a shell of immobilized analyte, hapten, or analyte-carrier protein conjugate attached to the particle by covalent bonds or physical adsorption; "analyte-carrier protein conjugate" is a compound in which an analyte molecule is covalently attached to a protein, e.g., human serum albumin (HSA); to form a "conjugate" which can be attached to a particle by covalent bonds or physical adsorption; "aggregation" is a process whereby individual reagent particles are linked together by analyte-specific antibody to produce dimer particles, trimer particles, and higher order networks of aggregated particles.

The present method may be applied to the detection of any analyte for which a specific antibody exists. The antibody may consist of whole antiserum, an IgG fraction, as affinity purified monospecific material, or a monoclonal derived material. The quantitative measurement aspect of the invention results from the fact that analyte present in the test sample and insolubilized analyte on the surface of particle reagent react competitively with analyte-specific antibody added in known amount to a reaction mixture. The greater the amount of analyte present in the test sample, the less antibody available for linking particle reagent to induce aggregation, and the greater the inhibition of particle reagent aggregation. The resulting aggregation is therefore related to the amount of analyte initially present in the test sample, e.g., by the decrease in the number of monomer particles (monomers) at a given time or by their initial rate of decrease, by the increase in the number of dimer particles at a given time or by their initial rate of increase, or by the distribution of various size particles at a given time after combining antibody and particle reagent with the analyte test sample to form a reaction mixture.

Various mixing protocols and contacting times of the reagents may be employed. Reagents can be contacted sequentially, or simultaneously at temperatures in the range of from about −5° to 50° C. and at a pH in the range of about 5–10, usually 6–8. Analysis of unknown amounts of a given analyte will usually be by comparison with a standard curve relating analyte concentration with the appropriate particle distribution property described above under the same conditions of time intervals and reagent amounts.

Analyte

This invention can be applied to the detection and measurement of a broad variety of analytes to which binding agents are available such as drugs of biological and clinical importance, metabolites, vitamins, pesticides, steroids, peptide hormones and certain cancer markers.

Analytes of particular interest include those drugs and hormones with either very low concentrations in biological fluids or with narrow therapeutic ranges. The cardiac steroid digoxin satisfies both criteria since levels below 0.8 ng/mL (nanograms per milliliter) in human serum are ineffective for treating cardiac arrhythmia while levels above 2.0 ng/mL are often toxic. Other analytes similarly present at low concentration or with narrow therapeutic range include vitamin $B_{12}$, folate, and most of the steroid, peptide, and protein hormones. Analytes such as myoglobin normally have very low levels in serum that can rise dramatically after myocardial infarction and are therefore indicative of this condition. Analytes such as microbial and cancer cell markers would generally be low in concentration since early detection (prior to prolonged cell growth) is highly desirable. Aminoglycoside drugs, barbiturate drugs, and many of the miscellaneous drugs such as theophylline are relatively high in concentration with $\mu$ g/mL (microgram/milliliter) levels but have narrow therapeutic ranges. Table I lists a variety of analytes of particular interest in practicing the instant invention.

TABLE I
ANALYTES

| | |
|---|---|
| Alkaloid Drugs | Steroids |
| benzoyl ecgonine | adrenocorticol steroids |
| cocaine | androgens |
| codeine | bile acids |
| dextromethorphan | digoxin |
| heroin | digoxigenin |
| lysergic acid | diethylstilbestrol |
| morphine | estrogen |
| quinidine | gestrogen |
| quinine | Toxins in Food |
| Aminoglycoside Drugs | aflatoxins |
| amikacin | ipomeamerone |
| gentamicin | mycotoxins |
| kanamicin | Toxics in Food |
| neomicin | ochratoxin |
| tobramicin | patalin |
| Antibiotic Drugs | penicillic acid |
| actinomycetin | tricothecene toxin |
| caromycin | zearclonone |
| chloramphenicol | Vitamins |
| chloromycetin | biotin |
| chlortetracycline | folic acid |
| erythormycine | thiamine |
| oxytetracycline | vitamin A |
| penicillin | vitamin $B_2$ |
| polymyxin B | vitamin $B_6$ |
| terramycin | vitamin $B_{12}$ |
| tetracycline | vitamin C |
| streptomycin | vitamin D |
| Barbiturate Drugs | vitamin E |
| diphenylhydantoin | Vitamin K |
| ethsuximide | Protein Hormones |
| phenobarbital | chorionic gonadotropin |
| primidone | chorionic thyrotropin |
| secobarbitol | glucagon |
| Marijuana Derivatives | insulin |
| cannabinol | nerve growth factor |
| tetrahydrocannabinol | parathyroid hormone |
| Metabolites | placental lactogens |
| galactose | prolactin |
| phenylpyruvic acid | proinsulin |
| porphyrin | relaxin |
| spermine | Proteins |
| Miscellaneous Drugs | albumin |
| amitriptyline | $\alpha_1$-acid glycoprotein |
| anticholinergic drugs | $\alpha_1$-antitrypsin |
| antihistimines | $\alpha_1$-glycoprotein |
| atropine | $\alpha_1$-lipoprotein |
| butyrophenones | $\alpha_2$-antitrypsin |
| caffeine | $\alpha_2$-macroglobulin |
| carbamazepine | $\alpha_2$-glycoprotein |
| chloropromazine | $\alpha_2$-lipoprotein |
| epinephrine | $\beta$-lipoprotein |
| griseofulvin | $\beta$-glycoprotein |
| imipramine | c-reactive protein |
| L-dopa | ferritin |
| lidocaine | fibrin split products |
| meperodine | fibrinogen |
| meprobamate | immunoglobulin A |
| methadone | immunoglobulin D |
| N—acetyl procainamide | immunoglobulin E |
| narceine | immunoglobulin G |
| nortriptyline | immunoglobulin M |
| oxazepam | haptoglobin |
| papaverine | hemoglobin |
| procainamide | ceruloplasmin |
| propanolol | cholinesterase |
| prostaglandins | hemopexin |
| tegretol | myoglobin |
| theophyline | rheumatoid factor |
| serotonin | thyroxine-binding globulin |
| valproic acid | transferrin |
| Peptide Hormones | transcortin |
| adrenocorticotropin (ACTH) | plasminogen |
| angiotensin | specific antibodies |

TABLE I-continued
ANALYTES

| | |
|---|---|
| met- and leu-enkephalin | coagulation factor |
| oxytocin | Microbial Surface Markers |
| thyroxine | bacterial antigens |
| triiodothyronine | fungal antigens |
| vasopressin | parasitic antigens |
| Pesticides | viral antigens |
| carbamate pestcides | Cancer Cell Markers |
| thiophosphate pesticides | carcinoembryonic antigen |
| polyhalogenated biphenyl pesticides | gangliosides |
| polyhalogenated sulfonamide pesticides | |

Antibody

Analytes and their specific antibodies rapidly interact and combine to form a tightly bound complex. Antisera for the analytes shown above are known. Generally, the smaller analytes (molecular weight less than 5000 daltons) are haptenated (covalently conjugated in immunologically active form), to proteins like human or bovine serum albumin to produce immunogen. The antibody can be used in this assay as a serum fraction, as an immunopurified monospecific antibody fraction, or as monoclonal antibody. The preparation of these various antibody fractions are well known in the literature. [Weir, D. M., Handbook of Experimental Immunology, Blackwell Science Publication, Oxford 1978, pp 6.1 to 10.5.]

Particle Reagent

The preparation of the particle reagents can be carried out as follows: The analyte or proteinaceous material, for example, can be adsorbed onto the surface of a polymer particle, followed by the reaction of a functional group on the surface of the polymer particle, for example, an epoxide group, under suitable pH conditions, with the complementary functional group of the analyte or the proteinaceous material. Any unreacted material is then separated from the particle reagent. The conditions of the reaction are such that there should be no substantial crosslinking of particles occurring.

Two ways of preparing a particle reagent which contains a compound of biological interest covalently attached through a proteinaceous material are preferred. The compound of biological interest, such as an analyte, can first be attached to the carrier protein and then attached to the polymer particle. Alternatively, the protein can first be attached to the polymer particle and then the analyte can be attached to the protein. The second approach has the advantage of using the same protein-particle reagent for the synthesis of particle reagents having a variety of compounds of biological interest attached to them.

The surface concentration of analyte or analyte-carrier protein conjugate on the polymer particle can be varied by reaction time, by dilution of the compounds of biological interest with an inactive diluent or by an additive which aids in the dispersion of the particles. While maximum surface concentration can yield fast agglutination rates, lesser surface concentration can be important in increasing assay sensitivity.

The resulting particle reagent can be suspended in a substantially aqueous medium which can further contain buffer, serum components and surfactants to yield a dispersed monomer particle reagent for use in light scattering immunoassay.

Instrumentation

The measurement of particle size distribution and its change with time is carried out by monitoring laser radiation scattered from individual particles and aggregated particles using an optical cuvette and photomultiplier-based detector system to record and analyze the scattered light.

Particle size analysis and counting instruments based upon light scattering techniques adapted to count particles entrained in aerosol and translucent fluid medium (primarily liquid) flows are known. Exemplary of such apparatus is that sold by Polytec Optronics, Incorporated of El Toro, Calif. as model HC15. It is often of advantage to obtain a histogram by count or other representation of the number of particles having sizes that are small as compared to the illuminating wavelength and/or that have an index of refraction close to the index of refraction of the medium. However, such apparatus as is commercially available is not believed able to provide quantitative measurements of the number of particles having such sizes or indices of refraction.

The Mie Theory relates to the radiation scattering properties of particles that are small as compared to the free space wavelength of the incident radiation. See, generally, Kerker, "The Scattering of Light and Other Electromagnetic Radiation", Academic Press, Inc. (1969). For purposes of this application, the term "size parameter" of a particle may be assigned the character "$\alpha$" and is defined by Mie as follows:

$$\alpha = \frac{2\pi}{\lambda_o} m_2 \delta \qquad (1)$$

where
$m_2$ is the index of refraction of the medium in which the particle is entrained,
$\delta$ is the radius of the particle, and
$\lambda_o$ incident radiation on the particle.

The term "relative refractive index" is assigned the character "m" and may be defined as follows:

$$m = \frac{m_1}{m_2} \qquad (2)$$

where $m_1$ is the index of refraction of the particle.

The term "sensitivity limit of detection" of a particle is assigned the character "S" and may be defined as follows:

$$S = |(m-1)|\alpha \qquad (3)$$

It is believed advantageous to provide a particle counting apparatus adapted to count particles each having an index of refraction close to that of the medium in which it is entrained and a radius on the order of 0.05 micrometers. In terms of The Mie Theory, for incident radiation with free space wavelength on the order of 0.633 micrometers, $m_1$ on the order of 1.59 and $m_2$ on the order of 1.33, such a particle has a sensitivity limit of detection S of at least 0.129.

Shown in FIG. 1 is a stylized pictorial representation of a particle counting apparatus generally indicated by reference character 10 in accordance with the present invention. The particle counting apparatus 10 includes a source 15 of collimated radiation at a predetermined wavelength (typically 0.633 micrometers), a cuvette or sample cell 16 through which flows a carrier fluid medium stream having particles to be counted entrained therein, and a detector 17 responsive to the intensity of radiation scattered by each particle in the stream to generate an electrical signal functionally related to the size thereof. A counter network 18 is operatively associated with the detector 17 to provide a count of the number of particles in the stream that fall within a predetermined size range. The cuvette 16 in accordance with this invention is disposed at the intersection of a first (incident) optical path generally indicated by reference character 22 and a second (collection) optical path generally indicated by reference character 24. The incident path 22 is preferably, but not necessarily, perpendicular to the collection path 24.

The first optical path 22 includes the radiation source 15. The source 15 produces the collimated radiation (indicated by reference character 25) which is directed toward a focusing objective lens 28. The objective lens 28 focuses the radiation, as shown by reference character 29, toward the cuvette 16. These elements, in cooperation with the geometry of the cuvette 16 to be discussed herein, serve to optically define and brightly illuminate a generally cylindrical viewing zone 30 (seen in FIG. 3) defined in the interior of the cuvette 16. In accordance with the present invention the viewing zone 30 exhibits a volume of about one picoliter (i.e., $10^{-12}$ liters). This volume corresponds to the volume of a cube 0.1 mm on a side. By keeping the volume of the viewing zone 30 as small as practicable, the radiation collected by the detector 17 from Rayleigh scattering due to the carrier fluid medium (typically water, $m_2=1.33$) in the viewing zone 30 is reduced. Thus, a relatively high particle density fluid stream (on the order of $10^{11}$ particles/liter) having particles each with a size (i.e., radius) that ranges as low as 0.05 micrometers, having an index of refraction on the order of 1.59 ($m_1=1.59$) and thus a sensitivity limit of detection S (as defined above) of at least 0.129 may be detected, resolved and counted. Moreover, the small dimensions of the viewing zone 30 reduces the probability of simultaneously detecting two particles in the viewing zone. Preferably the source 15 is a laser, such as a two milliwatt helium-neon apparatus, which provides intense diffraction-limited illumination of the viewing zone 30. Of course, any suitable source of intense diffraction-limited illumination may be utilized.

The second optical path 24 includes a positive objective lens 34 which collects radiation scattered in a cone as indicated by reference character 35. The objective lens 34 focusses and directs the collected radiation, as shown by reference character 36, toward a slit mask 37 disposed in front of the detector 17. These elements cooperate with the geometric configuration of the cuvette 16 to collect radiation scattered in the cone 35 with a relatively large (0.4) numerical aperture 40.

Referring to FIGS. 2A and 2B shown respectively are a plan and a side elevational view of a cuvette 16 in accordance with the present invention. The cuvette 16 is a substantially cylindrical member fabricated of Pyrex ® glass although any material that is transparent to the radiation emitted by the source 15 and scattered by the particles may be used. The material used to fabricate the cuvette 16 exhibits an index of refraction that is selected to be close to the index of refraction of the carrier fluid medium in which the particles are entrained so as to minimize internal reflectance of scattered light at the interface between the cuvette and the medium. The cuvette may be fabricated in any suitable manner, including injection molding.

A smooth bore 16B extends through the cuvette 16 to define a flow channel through which the carrier fluid medium carrying the particles to be counted may pass. The axis 16A of the bore 16B is parallel to the direction of fluid flow (i.e., perpendicular to the plane of FIG. 1). Preferably the axis 16A is coincident with the axis of the cuvette 16. The length of the cuvette 16 should be at least about ten times and is preferably, but not necessarily, about twenty-five times the diameter of the bore 16B.

The exterior of the cuvette 16 which is presented to the first optical path 22 is provided with a planar flattened portion 16F. This flattened portion 16F is provided with an optically smooth surface. The portion 16F extends for a distance along the height of the cuvette 16 sufficient to permit substantially aberration free illumination of the viewing zone 30 by radiation introduced thereinto from the source 15 along the first optical path 22. The exterior surface of the cuvette 16 is also provided with an indented cylindrical notch 16N. The cylindrical surface of the notch 16N has an axis 16S that is preferably oriented at a right angle to the axis 16A of the bore 16B. In the preferred case where the incident optical path 22 is perpendicular to the collection optical path 24 the axis 16S of the surface of the notch 16N also extends perpendicularly to the surface of the flattened portion 16F. Of course, this relationship is suitably modified to conform to the angle between the incident and collection paths. The radius 16R of the cylinder on which lies the surface of the cylindrical notch 16N is typically larger than the radius of the bore 16B. The dimension of the radius 16R of the indented cylindrical surface 16N is selected by geometric ray tracing techniques based upon the refractive indices of the carrier fluid medium and the material of the cuvette 16 to permit near aberration free collection of the radiation scattered from the particles passing through the viewing zone 30.

The cylindrical notch 16N compensates for the astigmatism introduced into the portion 35 of the collection optical path 24 by the differences in indices of refraction of the cuvette 16 and the carrier fluid medium and by the curvature of the bore 16B. Correction for this astigmatism is best done relatively near to the bore 16B and is necessary only in the collection optical path 24 due to the relatively large numerical aperture (i.e., 0.4) of the portion 35 of the collection path 24 as compared to the numerical aperture of the portion 29 of the incident optical path 22 (numerical aperture typically 0.02). The cylindrical notch 16N is sized so that the positive objective lens 34 may be inserted into the notch 16N and positioned close to the bore 16B. The concave surfaces of the cylindrical bore 16B and of the notch 16N form an orthogonal pair of negative cylindrical optical surfaces adapted to provide a numerical aperture of at least 0.4 to the objective 34. This large humerical aperture enables one to observe radiation scattered from a small particle over a wide range of angles to thereby enhance the detectability of such a particle.

The operation of the system 10 utilizing the particle counting apparatus 12 having the cuvette 16 therein for such an immunoassay is schematically shown in FIG. 3. The carrier fluid medium having a random stream of monomer, dimer, trimer or N-mer sized particles is passed through the cylindrical bore 16B and through the viewing zone 30 optically defined therein. The index of refraction of the particles is close to the index of refraction of the carrier fluid medium. It is this condition, coupled with the small size of the particles, that makes their detection for counting purposes difficult. Typically, such particles have a sensitivity limit of detection S (as defined above) of at least 0.129.

The radiation from the source 15 is focused into the viewing zone 30 by the action of the objective 28 and the surface 16F on the cuvette 16. The radiation which is scattered by particles passing through the viewing zone 30 and which appears within the light collection cone 35 is collected by the combined effects of the elements of the optical collection system including the carrier fluid medium, the bore 16B, the notch 16N and the objective 34 (not shown in the schematic illustration of FIG. 3). The cone 36 represents only the scattered light which is incident upon the detector 17 and includes the illuminated viewing zone imaged on a slit in the mask 37 perpendicular to the optical axis (also not shown in the schematic illustration of FIG. 3). Thus, the intensity of the radiation scattered by particles in the viewing zone 30 and collected by the collection optics is in proportion to the magnification of the collection optics and to the width of the slit in the mask 37. Radiation passing through the slit in the mask 37 is detected by the detector 17, typically a photodetection assembly such as that manufactured and sold by RCA under model number PF1006.

The output of the detector 17 is a series of pulses 42 the amplitude of which is related to the size of the particles from which radiation is scattered and the duration t of which (FIG. 3) is related to the residence time of the particle in the viewing zone. When used to practice the process of this invention, monomer, dimer, trimer and N-mer particles generate pulses of respectively increasing amplitude. This characteristic provides a convenient way whereby a count of particles within each respective range of sizes may be obtained.

Accordingly, the output of the detector 17 is connected to the counter network 18 which includes four separate channels one channel (46M) for a monomer particle count; a second channel (46D) for a dimer particle count; a third channel (46T) for a trimer particle count and a fourth channel (46N) for an N-mer particle count. The detailed schematic diagram of a suitable counter network 18 is shown in FIG. 4. In FIG. 4 the dimer count channel 46D, which is a typical one of the channels 46, is illustrated in more detail.

The output of the detector 17 is amplified by an amplifier 48, such as a device manufactured by Texas Instruments and sold under model number TL080. The output of the amplifier 48 is applied to the inverting input of an FET operational amplifier 50 such as that manufactured by Burr-Brown and sold under model number 3550 configured as a differential amplifier. The threshold of the differential amplifier 50 is made variable to define a predetermined threshold for each channel under consideration by the inclusion of a potentiometer 52 connected to the noninverting input to the amplifier 50. The threshold is continuously adjusted to accommodate fluctuations in the detector output by the action of a compensating network 54 that includes an operational amplifier 54A, such as that sold by National Semiconductor under model number 741.

When the signal applied to the inverting terminal of the amplifier 50 exceeds the adjusted threshold level applied at its noninverting terminal, an output signal is generated and applied (after appropriate inversion and amplification by an amplifier 56) to a monostable multivibrator 58 such as that sold by Fairchild under model number 74121. The amplifier 56 is similar to the amplifier 48. The output of the device 58 is connected to a digital counter 60D such as that manufactured by Princeton Applied Research, Inc. under model number 1109.

Each channel 46 operates in an analagous manner to produce an output which increments an associated counter 60. However, due to the relationship of the signals produced by the detector 17, a pulse 42 produced by an N-mer particle will exceed the thresholds for each channel 46M, 46D, 46T and 46N and will simultaneously increment the respective counters 60 associated with each of those channels. The magnitude of a pulse produced by a trimer particle will increment the counters associated with the channels 46M, 46D and 46T. Similarly, a dimer particle results in the incrementing of the counters associated with channels 46M and 46D. A monomer particle increments only the counter associated with the channel 46M. Accordingly, to obtain a count of each particle in each size range, an array of arithmetic logic units 62 or other suitable functional elements is connected to provide signals indicative of the number of N-mers (the difference between the counters 60N and 60T), the number of trimers (the difference between the counters 60T and 60D) and the number of dimers (the difference between the counters 60D and 60M). The number of monomer particles is obtained directly from the counter 60M.

Of course, any alternative counting arrangement may be utilized and remain within the contemplation of the present invention. For example a suitably interfaced and programmed microcomputer controlled arrangement may be used to accomplish this task. Using a single comparator such as the comparator 50, the output of which is connected to a frequency-to-voltage converter and the noninverting input of which receives a programmable input threshold (both being read or varied, respectively, by the microcomputer) one could sweep through values of threshold and record resulting voltages to obtain a "greater than" plot of pulse heights for the sample. A frequency-to-voltage converter such as sold by Dynamic Measurements Corp. under model 9110 and a Digital Equipment Corp. MINC computer can be utilized. A suitable program in MINC Basic Language Version 2.0 is attached to and made part of this application.

From the foregoing it may be appreciated that a particle counting apparatus has been disclosed which is able to detect, resolve and count particles having a sensitivity limit of detection S, as defined above, of at least 0.129.

EXAMPLES

Unless specified otherwise, in all statements of assay conditions and preparation of reagents, temperature is expressed in °C. and concentrations referred to as percentages are by weight/volume. The International System of Units (SI) is used throughout.

EXAMPLE 1—MEASUREMENT OF DIGOXIN

(1a) Preparation of Polystyrene/Polyglycidyl Methacrylate Shell-Core Polymer Particle A 0.3 liter round-bottomed flask, equipped with a stirrer and a thermostated heating mantle, was used to prepare polymer particles by polymerization at 70° C. under a nitrogen atmosphere. The seed emulsion was prepared by adding 5.0 mL of styrene to 0.2 L of water containing 0.2 g of Aerosol OT-100 (a dioctyl sodium sulfonsuccinate, available from American Cyanamid Co.) and 0.2 g of potassium persulfate. After two hours, a monomer feed, consisting of 20 mL of styrene and 0.15 g Aerosol OT-100 was started at a rate of 0.2 mL/min. After the addition of monomer was completed, the emulsion was stored at 70° C. overnight to insure complete conversion of the styrene. The final solids content was 9.7%, the particle size of the core polystyrene emulsion (determined by turbidity measurements at 546 nm) was 0.11 $\mu$m, and the surface tension (determined by a tensiometer using the DuNoüy Ring method) was 37 dynes/cm$^2$.

(1b) Preparation of Digoxin-HSA Conjugate

Digoxin (2.40 g) was dissolved in 144 mL of absolute ethanol. 144 mL of 0.1 M sodium periodate was added dropwise with stirring and the reaction allowed to continue for 25 min at 30° C.. At this time, 3.264 mL of 0.1 M glycerol dissolved in water was added to stop the reaction. After 5 min, the reaction mixture was added dropwise to 3.6 g of HSA in 144 mL of deionized water (pH adjusted to 9.2 with 5% potassium carbonate). The pH was maintained at 9.0-9.5 with 5% potassium carbonate during the course of reaction (30 min, 25° C.). Sodium borohydride (1.272 g) was added and, after 3 h, the pH was adjusted to 6.5 with 3.65 M HCl. The solution was then dialyzed against deionized water. Following dialysis, the solution was concentrated to 130 mL with an Amicon concentrator with a PM 10 filter. The solution was then lyophilized to yield the digoxin-HSA conjugate. Analyses for digoxin content by a sulfuric acid charring procedure and for protein content by absorbance at 280 nm indicated a ratio of 13.5 digoxin molecules per HSA protein molecule.

(1c) Preparation of Covalently Attached Digoxin-HSA Particle Reagent

Six mL of the polymer particle preparation (10% solids) described in Example 1a above, was added dropwise with stirring and sonication to 1.2 L of a solution (0.3 M NaCl, 0.02 M phosphate, pH 9.7) containing 1 mg/mL digoxin-HSA conjugate.

The resulting suspension was stirred, sonicated, and heated (50° C. for 1 h). The suspension was then centrifuged for 7 h at 12,500 rpm using a Du Pont Sorvall ® Model RC-5B centrifuge and a GSA rotor to remove any unadsorbed conjugate. The particle pellet was resuspended in 500 mL of 0.1% sodium dodecyl sulfate (SDS) dissolved in buffer (0.3 M NaCl, 0.02 M phosphate, pH 9.7), heated to 50° C. for 1 h and centrifuged again using the same conditions. The particle pellet was resuspended again in 250 mL of 0.1% SDS, sonicated, and centrifuged for 2 h at 19,500 rpm using an SS 34 rotor.

(1d) Particle Counting Assay for Digoxin

The light scattering particle detector was calibrated by pumping polymer particle suspensions of a known uniform size through the cuvette and adjusting the output of the comparator to obtain a predetermined discrimination in the four (4) channels of a Princeton Applied Research Counter, Model 1109. As shown in Table II, five (5) polystyrene particle suspensions of different known sizes in 0.3 M NaCl, 0.1% SDS, 0.02 M phosphate and 0.01% sodium azide at pH 7.6 at 0.0025% solids were pumped through the scattering particle detector at a flux of 1 mL/min. Particle counting was for a 1 second interval.

TABLE II

| Polymer Particle Size ($\mu$m) | Detector Calibration | | | | |
|---|---|---|---|---|---|
| | | Channel Number Pulse-Counts | | | |
| | MV | 1 | 2 | 3 | 4 |
| .8 | 1500 | 2600 | 1600 | 1000 | 528 |
| .6 | 750 | 2000 | 1000 | 500 | 270 |
| .36 | 350 | 1570 | 400 | 17 | 9 |
| .21 | 250 | 4900 | 2100 | 200 | 10 |
| .1 | 80 | 1485 | 130 | 0 | 0 |

With the detector calibrated in this manner, pulse-counts from monomer particles as well as dimer, trimer, and N-mer particle aggregates were accurately resolved and recorded.

The measurement of the effect of digoxin on the aggregation of digoxin-HSA particle reagent was conducted by diluting 0.1 mL of a 1% solution of the dioxin-HSA particle reagent (prepared in Example 1(c) above) to a final volume of 10 mL using a buffer solution containing 0.3 M NaCl, 0.1% sodium dodecyl sulfate (SDS), 0.02 M phosphate, 0.01% sodium azide at pH 7.6 and 0, 6.5, or 200 ng/mL digoxin. The resulting suspension was sonicated for 10 seconds in a Cole-Parmer bench top sonicator. The initial absorbance at 340 nm was 0.112. Aggregation was initiated by addition of 20 $\mu$L of rabbit anti-digoxin antibody (whole serum, Cappel Laboratories). At 0, 0.5, 2 and 4 minutes after addition of digoxin-specific antibody, 2 mL aliquots of the suspension were withdrawn and diluted 1:4 with a solution of 0.3 M NaCl, 0.1% SDS, 0.02 M phosphate, and 0.01% sodium azide at pH 7.6. Dilution in such medium effectively stops the aggregation process. These samples were pumped through the scattering particle detector as described above.

FIG. 5 illustrates the change in the number of monomer particles as well as dimer and trimer particle aggregates as a function of time in the presence of 0, 6.5 ng/mL digoxin, and 200 ng/mL digoxin. As can be seen, the concentration of monomer particles declines rapidly while the concentration of dimer particles and trimer particles increases. The change in monomer and dimer particle concentrations, especially, can be discerned before there is any appreciable change in the turbidity of the suspension. The greater the digoxin concentration, the greater the inhibition of the resultant aggregation.

The number of dimer particles at a given point in time can be used to determine the amount of digoxin which is present in a sample. Table III compares the number of dimers at the three different levels of digoxin, 0, 6.5, and 200 ng/mL, at t=0.5 minutes.

TABLE III

Correlation of Digoxin Amount with Particle Reagent Aggregation Properties

| Concentration ng/mL | Digoxin Number of dimers at 0.5 min |
|---|---|
| 0 | $8.2 \times 10^3$ |
| 6.5 | $6.2 \times 10^3$ |
| 200 | $0.3 \times 10^3$ |

By correlating the number of dimer particles present at 0.5 minutes with that present under known standard conditions, one can determine the amount of digoxin in unknown test samples.

It will be apparent that the instant specification and examples are set forth by way of illustration and not limitation, and that various modifications and changes may be made without departing from the spirit and scope of the present invention.

What is claimed is:

1. A method for determining the amount of an analyte in liquid medium comprising the steps of:
    A. contacting said liquid medium with reagents including:
        (1) analyte specific antibody, and
        (2) insoluble particles coated with analyte to form an aggregating reaction mixture comprisng said particles and different sized aggregates thereof;
    B. flowing said reaction mixture through an optically defined viewing zone upon which focused laser radiation is incident such that individual insoluble particles or individual aggregates thereof flowing through said zone produce discrete pulses of scattered radiation, each of said pulses having a magnitude which is a function of the size of the particle or individual aggregate from which the radiation was scattered;
    C. collecting said discrete pulses of radiation scattered from said viewing zone in a volume defined by a cone having an apex at said viewing zone and having a central axis substantially perpendicular to the incident focused laser radiation; and
    D. analyzing said discrete pulses of scattered laser radiation to determine the size distribution of said insoluble particles and individual aggregates thereof in said reaction mixture as a function of time subsequent to contacting said liquid medium with said reagents thereby determining the amount of said analyte initially present in said liquid medium.

2. The method of claim 1 wherein the analyte is a drug, metabolite, hormone, steroid, pesticide, environmental pollutant, food toxin, vitamin, protein, microbial surface marker, cancer cell marker, fungus, protozoan, virus, cell or tissue antigen.

3. The method of claim 2 wherein the analyte is a drug.

4. The method of claim 3 wherein the drug is digoxin.

5. The method of claim 1 wherein said optically defined viewing zone comprises a cuvette formed from a material transparent to collimated radiation at a predetermined wavelength and exhibiting an index of refraction close to the index of refraction of the medium, the cuvette having a cylindrical bore extending therethrough, the axis of the bore being parallel to the direction of the particle flow through the cuvette, the cuvette having a cylindrical surface on the exterior thereof, the axis of the cylinder on which the surface lies being perpendicular to the axis of the bore.

6. The method of claim 1 wherein the change in the distribution of aggregate size as a function of time subsequent to contacting said liquid medium with said reagents is utilized for determining the amount of said analyte initially present in said liquid medium.

7. The method of claim 1 wherein the concentration of a particular size aggregate at a given time subsequent to contacting said liquid medium with said reagents is utilized for determining the amount of said analyte initially present in said liquid medium.

8. The method of claim, 1 wherein the rate of formation of a given size aggregate subsequent to contacting said liquid medium with said reagents is utilized for determining the amount of said analyte initially present in said liquid medium.

9. The method of claim 1 wherein the steady-state maximum concentration of a given size aggregate subsequent to contacting said liquid medium with said reagents is utilized for determining the amount of said analyte initially present in said liquid medium.

10. The method of claim 1 wherein the concentration of dimer particles at a time of from 0.5 minutes to 2.0 minutes subsequent to contacting said liquid medium with said reagents is utilized for determining the amount of digoxin initially present in said liquid medium.

11. The method of claim 1 wherein the concentration of reagent particles relative to the concentration of an aggregate of a preselected size at a given time subsequent to contacting said liquid medium with said reagents is utilized for determining the amount of said analyte initially present in said liquid medium.

* * * * *